United States Patent [19]

Romaniszyn et al.

[11] Patent Number: 4,984,582
[45] Date of Patent: Jan. 15, 1991

[54] VACUUM ASSISTED CONDOM APPLICATOR

[76] Inventors: Gregory Romaniszyn; Eva Romaniszyn, both of 339 Cornwall Drive, Fort McMurray, Alberta, Canada, T9K 1C6

[21] Appl. No.: 531,147

[22] Filed: May 31, 1990

[51] Int. Cl.$^5$ ............................................. A61F 6/04
[52] U.S. Cl. ................................. 128/844; 604/346; 604/349
[58] Field of Search ................ 128/844; 604/346, 349, 604/347; 2/21

[56] References Cited

U.S. PATENT DOCUMENTS

| | | | |
|---|---|---|---|
| 4,840,187 | 6/1989 | Brazier | 128/844 |
| 4,867,176 | 9/1989 | Lash | 128/830 |
| 4,872,463 | 10/1989 | Nishizono | 128/844 |
| 4,875,491 | 10/1989 | Parrone | 128/844 |

Primary Examiner—Mickey Yu
Assistant Examiner—Kerry Owens
Attorney, Agent, or Firm—Fleit, Jacobson, Cohn, Price, Holman & Stern

[57] ABSTRACT

A vacuum assisted condom applicator is provided made out of a suitable plastic material in the form of a rigid, or semirigid, double walled tube, open at one end and closed with a spherical cap on the other end to define an inner space. An internal space provided between the double walls of the tube and the cap is connected to the inner space by means of many small holes. A lower part of an outside wall surface of the invention is equipped with a normally closed membrane valve, which includes a push button release. The spherical top of the invention is equipped with a membrane valve which is closed and sealed by the factory at which a condom is prestretched and packed within the double walled tube. Each individual condom is factory prestretched and evenly lined along an inner surface of the double walled tube and held in place by a vacuum created in a space between the double walls of the tube. A large number of small holes allows for a sensitive application of the vacuum forces to the outer surface of the condom. The membrane valve button is then depressed to instantly allow air through the membrane valve button into the evacuated space between the double walls to thereby release the condom from the inner wall of the tube and thereafter remove the empty double walled tube.

5 Claims, 1 Drawing Sheet

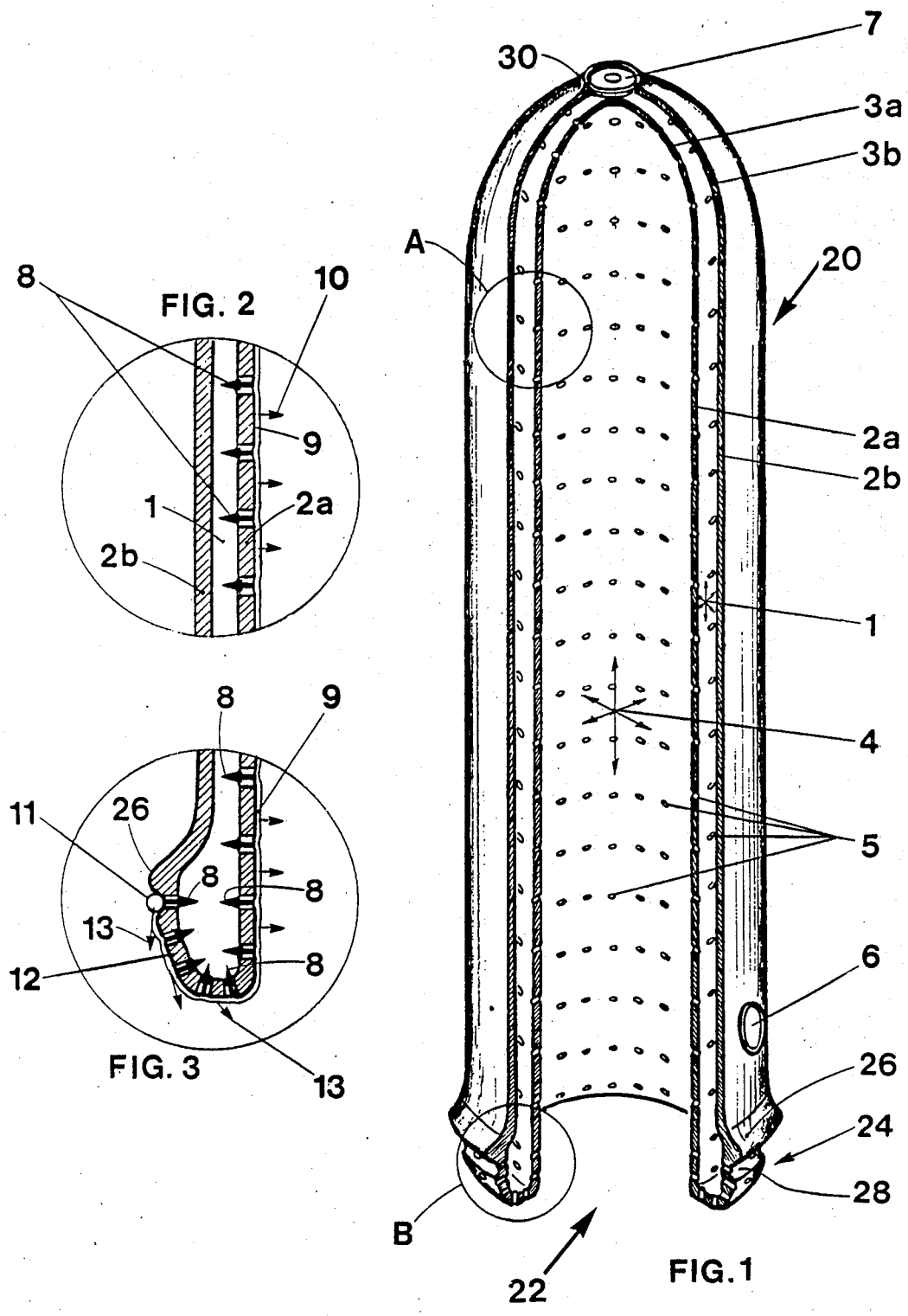

VACUUM ASSISTED CONDOM APPLICATOR

FIELD OF THE INVENTION

A vacuum assisted condom applicator is used to release an unrolled condom onto at least a partially erect penis.

BACKGROUND OF THE INVENTION

Presently condoms are available in the form of a rolled ring, which must be turned up in a way which would allow unrolling. The unrolled condom is positioned on the top of a well erected penis and carefully rolled down the penis.

The present method of condom application has the following major limitations:
(1) requires well erected penis,
(2) requires proper identification of which side of the rolled condom ring should go up,
(3) requires sensitive fingers with well trimmed nails or a bright light and good vision,
(4) takes too much time,
(5) is inconvenient for women,
(6) creates risk of mechanical damage during application (nail cuts), and
(7) precludes instant verification for manufacturer's or storage defects.

SUMMARY OF THE INVENTION

An object of the present invention is to eliminate all the limitations described for previous methods of condom application.

The present invention is made out of a suitable plastic material in the form of a rigid, or semirigid, double walled tube, open at one end and closed with a double walled spherical cap on the other end to define an inner space. An internal space provided between the double walls of the tube and the cap is connected to the inner space by means of many small holes. A lower part of an outside wall surface of the invention is equipped with a normally closed membrane valve, which includes a push button release. The spherical top of the invention is equipped with a membrane valve which is closed and sealed by the factory at which a condom is prestretched and packed within the double walled tube.

Each individual condom is factory prestretched and evenly lined along an inner surface of the double walled tube and held in place by a vacuum created in a space between the double walls of the tube and double walls of the cap. A large number of small holes allows for a sensitive application of the vacuum forces to the outer surface of the condom.

All types of presently used condoms are suitable for factory attachment to the double walled tube of the invention. A condom attached to the inner surface of the inner wall of the double walled tube is ready for instant use.

With a single motion of one hand, a man or a woman can locate the double walled tube over a fully or partially erected penis. The membrane valve button is then depressed to instantly allow air through the membrane valve into the evacuated space between the double walls to thereby release the condom from the inner wall of the tube to the penis and thereafter the empty double walled tube is removed from the penis.

The mechanics of the double walled tube is based on the following principles.

The atmospheric air pressure allowed in the space provided between the double walled tube, by the means of opening the push button membrane valve, spreads instantly, eliminating vacuum between the walls and vacuum forces exerted to the condom through the large number of small holes. As a result the elasticity forces, existent in the prestretched condom, act instantly causing shrinkage of the condom, downslide of its outer ring along a conical rim located at a base of the double walled tube and even adherence of the condom to the penis.

It is an object of the invention to provide a vacuum assisted condom applicator having a double walled tubular shape with a double walled spherical cap on one end, an internal space provided between the double walls of the tube and the cap, and a large number of small holes extending through an innermost internal wall.

It is another object of the invention to provide a vacuum assisted condom applicator having a double walled tubular shape with a double walled spherical cap on one end, an internal space provided between the double walls of the tube and the cap, and a large number of small holes extending through an innermost internal wall with an application of a vacuum in the internal space for holding a prestretched, ready-to-use condom lined along the innermost internal wall.

It is yet another object of the invention to provide a vacuum assisted condom applicator having a double walled tubular shape with a double walled spherical cap on one end, an internal space provided between the double walls of the tube and the cap, and a large number of small holes extending through an innermost internal wall with an application of a vacuum in the internal space for holding a prestretched, ready-to-use condom lined along the innermost internal wall by the small holes, sealed by an attached outer surface of the prestretched condom.

It is still yet another object of the invention to provide a vacuum assisted condom applicator having a double walled tubular shape with a double walled spherical cap on one end, an internal space provided between the double walls of the tube and the cap, and a large number of small holes extending through an innermost internal wall with an application of a vacuum in the internal space for holding a prestretched, ready-to-use condom lined along the innermost internal wall by the small holes, sealed by an attached outer surface of the prestretched condom with application of atmospheric air pressure within the double walls for instant release of the condom.

These and other objects of the invention as well as many of the intended advantages thereof, will become more readily apparent when reference is made to the following description taken in conjunction with the accompanying drawings.

BRIEF DESCRIPTION OF THE DRAWINGS

FIG. 1 is a sectional view of a vacuum assisted condom applicator.

FIG. 2 is an enlarged sectional view of the area encircled as "A" in FIG. 1.

FIG. 3 is an enlarged sectional view of the area encircled as "B" in FIG. 1.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general, and to FIG. 1, in particular, a vacuum assisted condom applicator embodying the teachings of the subject invention is generally designated as 20. With reference to its orientation in FIG. 1, the applicator 20 comprises a double-walled cap having inner wall 3a and outer wall 3b, which are continuous with a double-walled tube having inner wall 2a and outer wall 2b. The applicator 20 is shown in FIG. 1 in partial section, it being understood that the tubular portion having inner and outer walls 2a and 2b is cylindrical having an opening 22 at one end and having a cap at the opposite end formed by inner and outer walls 3a, 3b.

Defined within the interior of inner walls 3a and 2a is inner space 4. An internal space 1 formed between the walls 2a, 2b and 3a, 3b communicates with the inner space 4 through a plurality of small holes 5 defined in the inner wall 2a, 3a, throughout the entire inner space 4 and partially around a lowermost portion 24 of the outer wall 2b as limited by an annular ridge 26.

Located slightly above annular ridge 26 in outer wall 2b is a push-button membrane valve 6 which acts as a check valve for only letting air from outside wall 2b into the internal space 1 upon depression of the valve 6. In its normal position, the valve 6 prevents the passage of air into or out of internal space 1.

For locating a condom 9 within the inner space 4, a condom is unraveled at the factory and located to lie along the interior surface of the inner wall 3a, 2a such that an outer ring 11 of the condom 9 is positioned within an annular groove 28 located adjacent to the annular ridge 26. The placed condom thereby lies from the apex 30 of the cap portion defined by inner and outer walls 3a, 3b into the groove 28.

Membrane valve 7 provides a one-way seal for evacuation of air from within internal space 1. The outer wall of the condom 9 is sucked during evacuation of the internal space 1 into the plurality of holes 5 spaced about the applicator 20 by a slight vacuum forces as indicated by arrows 8 in FIGS. 2 and 3. When a vacuum has been drawn on the internal space 1, such that the outer surface of the condom 9 is engaged within the plurality of holes 5 so as to hold the condom in place, the membrane valve 7 is closed and sealed at the factory to thereby hold a prestretched condom within the applicator 20. The internal dimensions of the inner space 4 is just slightly greater than the relaxed dimensions of the condom 9 so that upon sucking of the outer surface of the condom into the holes 5 the condom is in a slightly stretched condition which is allowed due to its inherent elasticity.

During use of the applicator, the applicator is located over a fully or partially erected penis. The membrane valve button 6 is then depressed to instantly allow air into the previously evacuated space 1 located between the inner and outer walls 2a, 2b and 3a, 3b. The introduction of air into the inner space 1 eliminates the vacuum forces 8 exerted to the condom through the plurality of holes 5. As a result of the elasticity forces 10 existent in the prestretched condom, when the vacuum is released, the whole condom contracts, while its outer ring 11 moves downward and away from the lowermost portion 12 of the applicator in the direction of arrows 13 towards its relaxed condition for simultaneous release of the prestretched condom to cause even adherence of the condom to the penis.

Therefore, by the use of the applicator of the present invention, the difficulties encountered in the prior procedures have been overcome with advantages previously not available.

Having described the invention, many modifications thereto will become apparent to those skilled in the art to which it pertains without deviation from the spirit of the invention as defined by the scope of the appended claims.

We claim:

1. A condom applicator comprising:
   a housing having an open end and an opposite closed end, said housing including an inner wall and an outer wall spaced from each other along a substantial portion of their length and interconnected to define an internal space therebetween, said inner wall including a plurality of holes to communicate the internal space with an interior of the housing,
   sealing means for sealing said internal space after said internal space has been evacuated to maintain a vacuum in the internal space by stretching a condom located in the housing against the inner wall of the housing to block said plurality of holes with the condom, and
   air inlet means for allowing air into the internal space so as to overcome the vacuum and release the condom.

2. A condom applicator as claimed in claim 1, wherein said air inlet means is a normally closed valve.

3. A condom applicator as claimed in claim 1, wherein said sealing means is a permanent sealing device for sealing the housing once a vacuum has been established in the internal space.

4. A condom applicator as claimed in claim 1, wherein said outer wall includes a groove for locating a rim of a condom.

5. In combination, a condom and a condom applicator, said condom applicator including a double-walled housing having an interior wall and an exterior wall with an internal space located therebetween with a plurality of holes located in said interior wall, said condom being located in intimate contact with said plurality of holes to maintain a vacuum in said internal space, and means for releasing the vacuum so that said condom is released from said condom applicator.

* * * * *